(12) United States Patent
Kim et al.

(10) Patent No.: US 10,835,294 B2
(45) Date of Patent: Nov. 17, 2020

(54) SPACER APPARATUS BETWEEN SPINOUS PROCESSES

(71) Applicant: Solco Biomedical Co., Ltd., Pyeongtaek si (KR)

(72) Inventors: Il Kim, Seoul (KR); Hyeun Sung Kim, Seoul (KR)

(73) Assignee: Solco Biomedical Co., Ltd., Gyeonggi-do (KR)

(*) Notice: Subject to any disclaimer, the term of this patent is extended or adjusted under 35 U.S.C. 154(b) by 0 days.

(21) Appl. No.: 16/280,263

(22) Filed: Feb. 20, 2019

(65) Prior Publication Data
US 2020/0261122 A1  Aug. 20, 2020

(51) Int. Cl.
*A61B 17/70* (2006.01)

(52) U.S. Cl.
CPC .................. *A61B 17/7062* (2013.01)

(58) Field of Classification Search
CPC ............ A61B 17/7062; A61B 17/7053; A61B 17/707
USPC ................................................. 606/249, 248
See application file for complete search history.

(56) References Cited

U.S. PATENT DOCUMENTS

| | | | | |
|---|---|---|---|---|
| 5,496,318 A | * | 3/1996 | Howland | A61B 17/7053 606/249 |
| 6,761,720 B1 | * | 7/2004 | Senegas | A61B 17/7053 606/249 |
| 7,588,601 B2 | * | 9/2009 | Le Couedic | A61B 17/7053 606/246 |
| 2007/0162005 A1 | * | 7/2007 | Peterson | A61B 17/7062 606/279 |
| 2008/0177306 A1 | * | 7/2008 | Lamborne | A61B 17/7062 606/246 |
| 2010/0204732 A1 | * | 8/2010 | Aschmann | A61B 17/7053 606/249 |
| 2011/0160772 A1 | * | 6/2011 | Arcenio | A61B 17/7053 606/248 |
| 2012/0109199 A1 | * | 5/2012 | Kothari | A61B 17/68 606/248 |
| 2012/0239089 A1 | * | 9/2012 | Druma | A61B 17/7068 606/249 |
| 2019/0099206 A1 | * | 4/2019 | Senegas | A61B 17/7064 |

* cited by examiner

*Primary Examiner* — Eduardo C Robert
*Assistant Examiner* — David C Comstock
(74) *Attorney, Agent, or Firm* — Kelly & Kelley, LLP

(57) ABSTRACT

Provided is a spacer apparatus between spinous processes including a spacer disposed between two mutually neighboring spinous processes of vertebrae, a band provided as a pair, bound respectively to the two mutually neighboring spinous processes and fixed to the spacer in end portion thereof to maintain the spacer between the two mutually neighboring spinous processes, a fixing cap coupled to the spacer to fix the end portion of the band to the spacer, and an elastic body mounted on the spacer and maintaining a coupling force between the spacer and the fixing cap.

7 Claims, 10 Drawing Sheets

SPACER APPARATUS BETWEEN SPINOUS PROCESSES

BACKGROUND OF THE INVENTION

Field of the Invention

The present invention relates to a spacer apparatus between spinous processes having a structure which may be easily and conveniently mounted in a patient's body.

Related Art

The contents described in this section merely provide background information regarding the embodiment and do not constitute the related art.

The spinal canal is a passage through which the spinal nerves pass and by which holes behind each vertebrae are connected vertically to form a tunnel through which the nerves extend from the brain to the arms and legs.

A problem in the vertebral may lead to exposure to diseases such as spinal stenosis that the spinal canal is narrowed to pressurize the spinal nerves causing a severe pain.

The most common spinal disease may be degenerative spinal stenosis.

The degenerative spinal stenosis is caused as a degenerated disk protrudes to press nerves on the front and a ligament flava that covers nerves is thickened and hardened to press the nerves on the rear, facet joints positioned on the rear side of the spinal canal are enlarged, and spinal nerves are pressed by the born (bony spur) abnormally grown out due to frictional contact of the vertebrae during an aging process of the spine.

Thus, in order to treat such degenerative spinal stenosis or other kinds of spinal diseases or to alleviate the symptoms of spinal diseases, an artificial device may be installed in the vertebrae by surgery in some cases.

The operation of inserting such an artificial device into a patient's body may cause severe pain or deterioration of health in the case of failure and result in a re-operation which is troublesome.

In particular, if an artificial device is mounted in a position adjacent to the human vertebrae, failure of surgery may cause fatal damage to the patient in terms of medical characteristics such as vertebrae bones, vertebral spinal nerve, and the like.

SUMMARY OF THE INVENTION

The present invention provides a spacer apparatus between spinous processes, having a structure which may be simply and conveniently mounted in a patient's body.

Technical subjects of the present invention are not limited to the foregoing technical subjects and any other technical subjects not mentioned may be clearly understood by a skilled person in the art from the following description.

In an aspect, a spacer apparatus between spinous processes includes: a spacer disposed between two mutually neighboring spinous processes of vertebrae; a band provided as a pair, bound respectively to the two mutually neighboring spinous processes and fixed to the spacer in end portion thereof to maintain the spacer between the two mutually neighboring spinous processes; a fixing cap coupled to the spacer to fix the end portion of the band to the spacer; and an elastic body mounted on the spacer and maintaining a coupling force between the spacer and the fixing cap.

The fixing cap may include: a cap body having a first through hole allowing the end portion of the band to pass therethrough; and a coupling part protruding from the cap body and coupled to the spacer, wherein the spacer has a second through hole allowing the coupling part to be inserted thereinto.

The first through hole may have a slit shape, may penetrate through the cap body, may be formed to be parallel to a longitudinal direction of the coupling part, and may be provided as a pair symmetrical to each other with respect to the coupling part.

The band may be disposed between the spacer and the fixing cap as the end portion thereof is inserted into the first through hole, and may be pressed by the spacer and the fixing cap so as to be coupled to the spacer in a state in which one surface of the band is in contact with one surface of the spacer and the other surface thereof is in contact with one surface of the fixing cap.

The spacer may include a first groove formed on an inner circumferential surface of the second through hole in a circumferential direction and allowing the elastic body to be seated therein, and the fixing cap may include a second groove formed on an outer circumferential surface of the coupling part in the circumferential direction and facing the first groove when the coupling part is inserted into the second through hole.

The elastic body may have a ring shape so as to be seated in a space formed by the first groove and the second groove, and when the coupling part is inserted into the second through hole, the elastic body may press the coupling part and the spacer to maintain a coupling force between the fixing cap and the spacer.

The fixing cap may have a guide recess as a portion where a surgical tool grips the fixing cap, wherein the guide recess is formed by being recessed a part of the cap body, and the guide recess is provided as a pair.

The spacer may have a seating recess provided as a pair at symmetrical positions on an outer circumferential surface thereof and allowing the mutually neighboring spinous processes to be seated thereon, respectively.

In another embodiment of the spacer apparatus between spinous processes, the fixing cap may include a through hole formed to penetrate through the centers of the cap body and the coupling part, and the spacer apparatus between spinous processes may further include: a guide wire disposed to be inserted into the second through hole and the third through hole.

DESCRIPTION OF EXEMPLARY EMBODIMENTS

Hereinafter, embodiments will be described with reference to the annexed drawings and description. However, the embodiments set forth herein may be variously modified, and it should be understood that there is no intent to limit the disclosure to the particular forms disclosed, but on the contrary, the embodiments are to cover all modifications, equivalents, and alternatives falling within the spirit and scope of the disclosure as defined by the claims.

It will be understood that, although terms "first", "second", etc. may be used herein to describe various elements, these terms do not limit the elements. These terms are used only to discriminate one substance or element from other substances or elements. Further, terms specially defined in consideration of the configurations and functions of the embodiments serve only to describe the embodiments and do not limit the scope of the disclosure.

In the following description of the embodiments, it will be understood that, when each element is referred to as being formed "on" or "under" another element, it may be directly "on" or "under" the other element or be indirectly formed with one or more intervening elements therebetween. Further, when an element is referred to as being formed "on" or "under" another element, not only the upward direction of the former element but also the downward direction of the former element may be included.

In addition, it will be understood that, although relational terms "on/above/upper", "under/below/lower", etc. may be used herein to describe various elements, these terms neither necessarily require nor connote any physical or logical relations between substances or elements or the order thereof, and are used only to discriminate one substance or element from other substances or elements.

Figure 1:
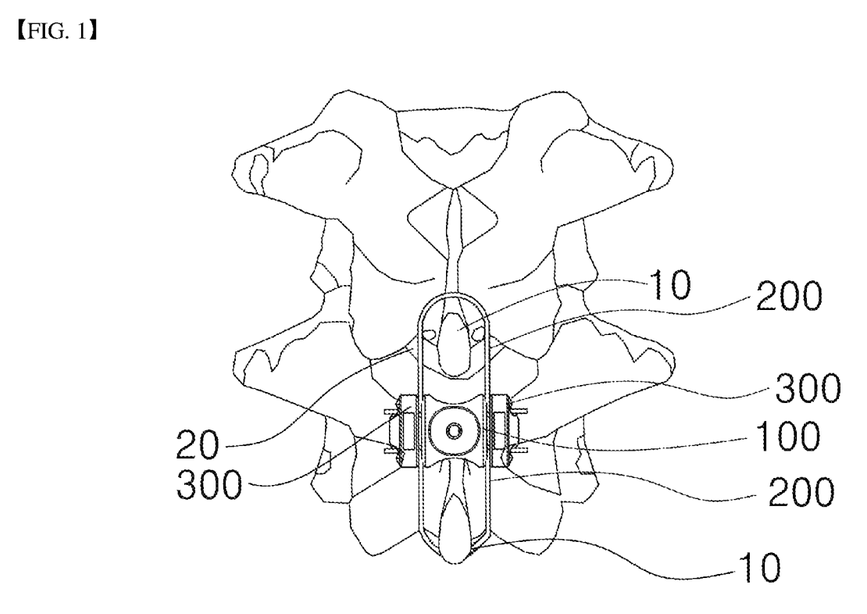
FIG. 1 is a view illustrating a state in which a spacer apparatus between spinous processes of an embodiment is coupled to vertebrae.
Figure 2:
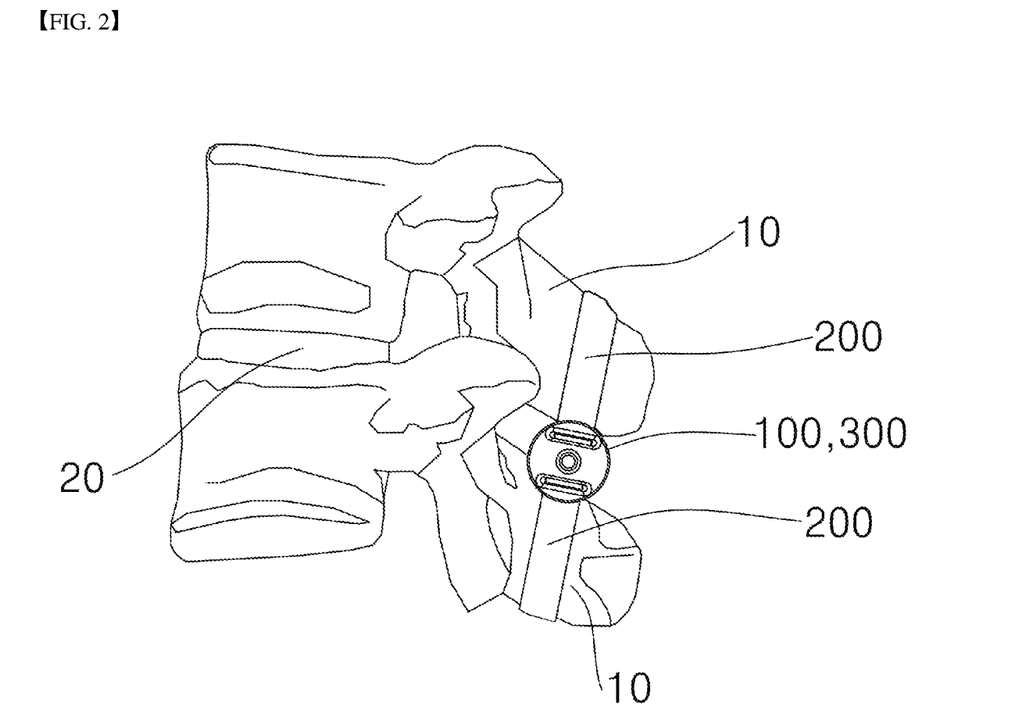
FIG. 2 is a side view of FIG. 1.

FIG. 1 is a view illustrating a state in which a spacer 100 apparatus between spinous processes 10 of an embodiment is coupled to vertebrae. FIG. 2 is a side view of FIG. 1.

The spacer 100 apparatus between the spinous processes 10 of the embodiment may be disposed between two mutually neighboring spinous processes of vertebrae to prevent the occurrence of disease due to protrusion of a disc 20 of a spine.

The vertebrae have the discs 20 present between a plurality of joints including the spinous processes 10 to connect the joints and allow the vertebrae to move flexibly.

For example, if the disk 20 degenerated due to aging of the spine protrudes, or if the disk 20 protrudes due to any other cause, to press spinal nerves positioned adjacent to the rear side of the disk 20, the patient may suffer a severe pain and have difficulty in normally moving his or her body.

Such protrusion of the disc 20 may be exacerbated as space between the mutually neighboring spinous processes 10 becomes narrower due to activity of the patient. That is, if the space between the mutually neighboring spinous processes 10 is narrowed, space between mutually neighboring joints including each process 10 may be narrowed.

Thus, the disc 20 between the joints is pressed by the joints and moves to protrude in a direction substantially perpendicular to a direction in which the disk 20 is pressed, and as a result, the disk 20 may press and stimulate spine nerves positioned at a spinal canal adjacent to the rear of the disk 20, i.e., the rear of the vertebrae.

Therefore, the spacer 100 apparatus between spinous processes 10 may be disposed between mutually neighboring spinous processes 10 to maintain space between the spinous processes 10, thus suppressing protrusion of the disk 20 caused as the space between the spinous processes 10 is narrowed and a resultant degradation of disease.

Figure 3:
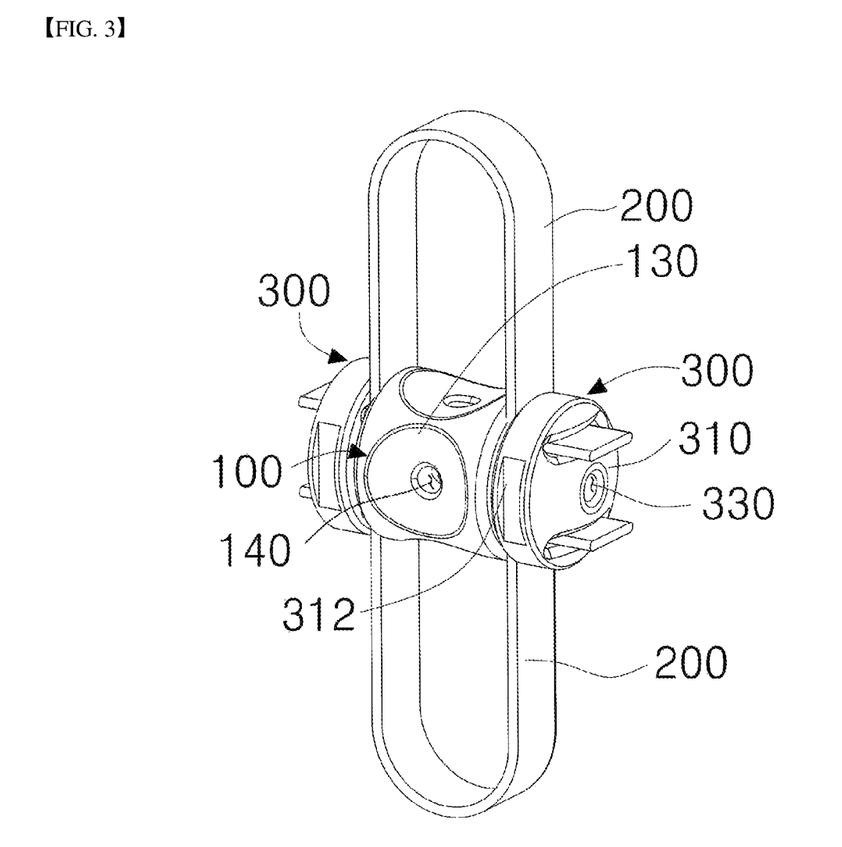
FIG. 3 is a perspective view illustrating a spacer apparatus between spinous processes of an embodiment.
Figure 4:
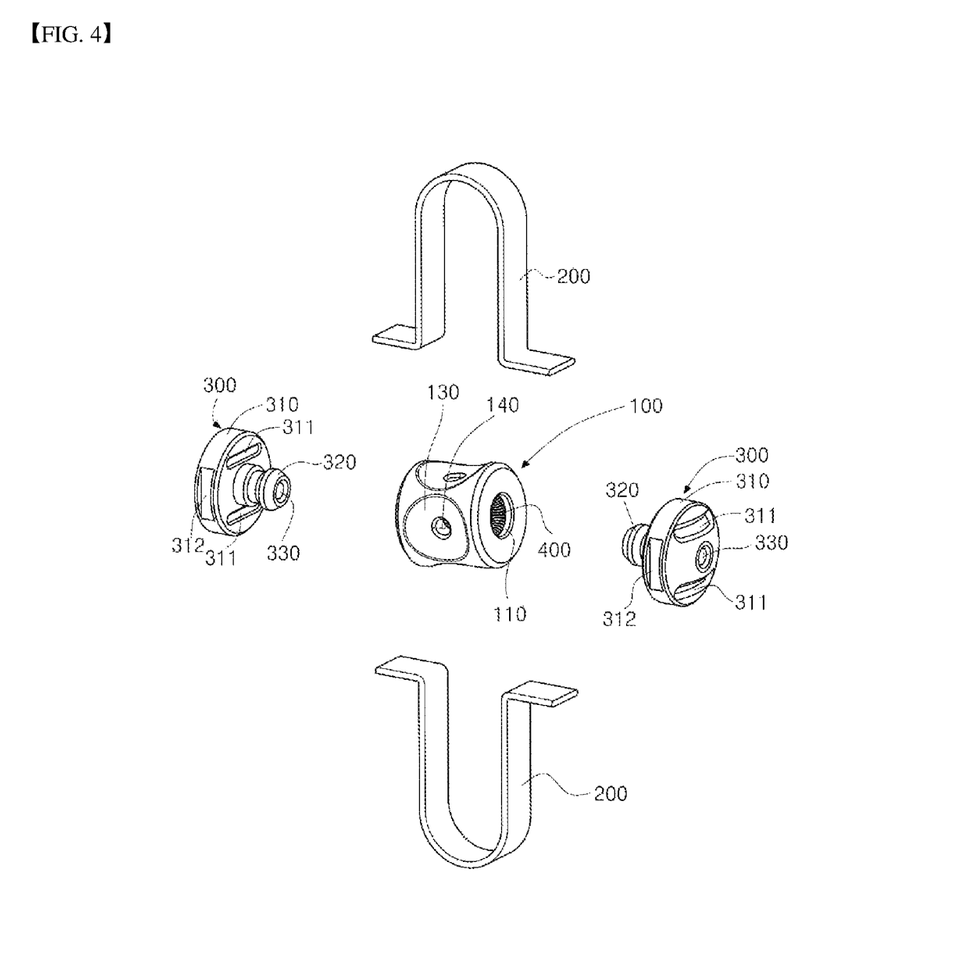
FIG. 4 is an exploded view of FIG. 3.
Figure 5:
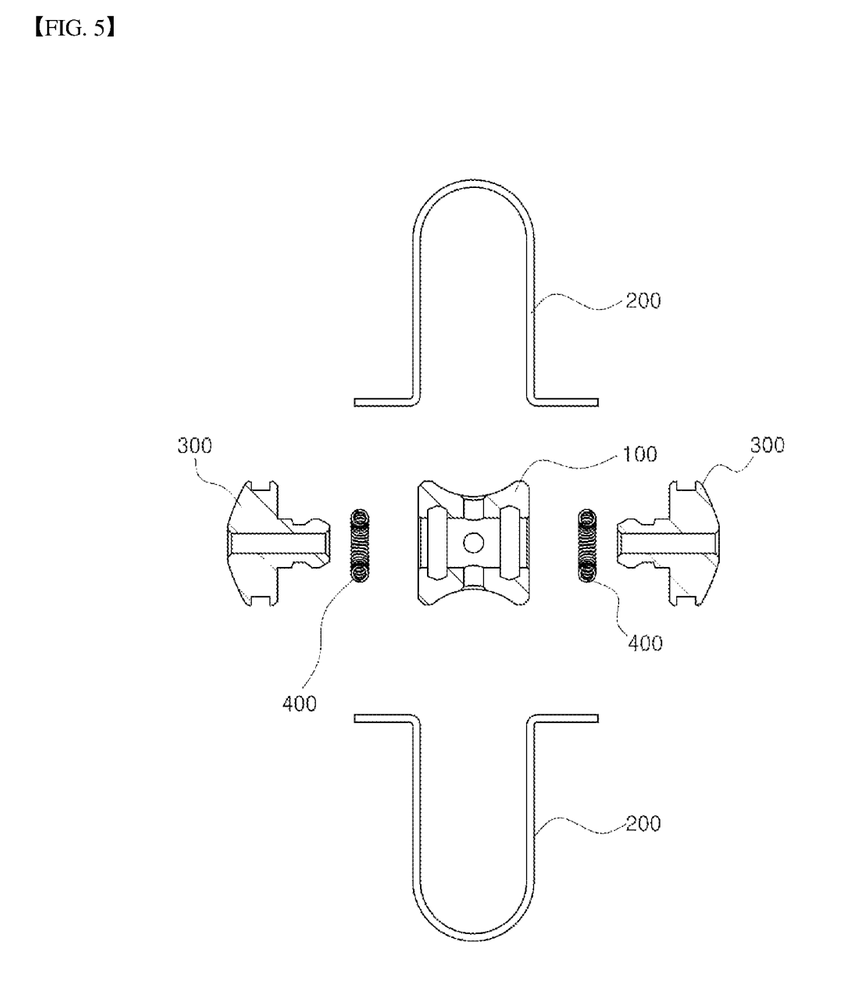
FIG. 5 is a disassembled cross-sectional view of a spacer apparatus between spinous processes of an embodiment.

FIG. 3 is a perspective view illustrating a spacer 100 apparatus between the spinous processes 10 according to an embodiment. FIG. 4 is an exploded view of FIG. 3. FIG. 5 is a disassembled cross-sectional view of the spacer 100 apparatus between the spinous processes 10 of an embodiment.

The spacer 100 apparatus between the spinous processes 10 may include the spacer 100, a band 200, a fixing cap 300, and an elastic body 400.

The spacer 100 apparatus between the spinous processes 10 may be inserted into a patient's body by surgery (i.e., an operation) and attached to the vertebrae. Thus, the spacer 100, the band 200, and the fixing cap 300 may be formed of a biocompatible material that does not cause an adverse reaction in the body when inserted into the body or has a very low adverse reaction.

In particular, the spacer 100 and the fixing cap 300 may be manufactured using bioplastics, specifically, polyetheretherketone (PEEK), as a solid biocompatible material.

The spacer 100 may be disposed between two neighboring spinous processes 10 of the vertebra. Each of the spinous processes 10 may come into contact with the spacer 100 disposed between the neighboring spinous processes 10, and thus, the spinous processes 10 may be spaced apart from each other by a width occupied by the spacer 100.

That is, although space between the two neighboring spinous processes 10 becomes narrow due to activity of the patient, the space between the spinous processes 10 is not narrowed any further to be less than the width occupied by the spacer 100 due to the spacer 100 disposed therebetween.

The band 200 is provided as a pair and the pair of bands are respectively bound to the two mutually neighboring spinous processes 10 and end portions of the bands 200 are fixed to the spacer 100, whereby the spacer 100 may be maintained between the two mutually neighboring spinous processes 10.

That is, as the pair of bands 200 are bound to the mutually neighboring spinous processes 10, respectively, the spacer 100 fixed therebetween is stably disposed between the spinous processes 10 and a decrease in space between the neighboring spinous processes 10 may be suppressed.

The fixing cap 300 may be coupled to the spacer 100 to fix the end portions of the bands 200 to the spacer 100. As illustrated in FIG. 3, the fixing cap 300 may be provided as a pair.

Here, the pair of fixing caps 300 may fix one end portions of the pair of bands 200 to the spacer 100, respectively. The pair of fixing caps 300 may be coupled to both sides of the spacer 100 to fix the pair of bands 200 to the spacer 100.

The elastic body 400 may be seated on the spacer 100 to maintain a coupling force between the spacer 100 and the fixing cap 300. That is, when the fixing cap 300 is inserted into the spacer 100 and pressed, the elastic body 400 is elastically deformed when a corresponding pressing force exceeds a predetermined force, allowing the fixing cap 300 to be stably mounted on the spacer 100, and accordingly, the band 200 may be fixed to the spacer 100.

In contrast, when the fixing cap 300, in a state of being stably mounted on the spacer 100, is pulled out by the predetermined force or greater, the elastic body 400 is elastically deformed to allow the fixing cap 300 to be separated from the spacer 100, and accordingly, the band 200 may also be separated from the spacer 100.

Here, the force for stably mounting the fixing cap 300 on the spacer 100 and the force for separating the fixing cap 300 from the spacer 100 may be equal or similar, and the spacer 100 apparatus between the spinous processes 10 may be designed such that the force is, for example, about 50N to 70N.

Figure 6:
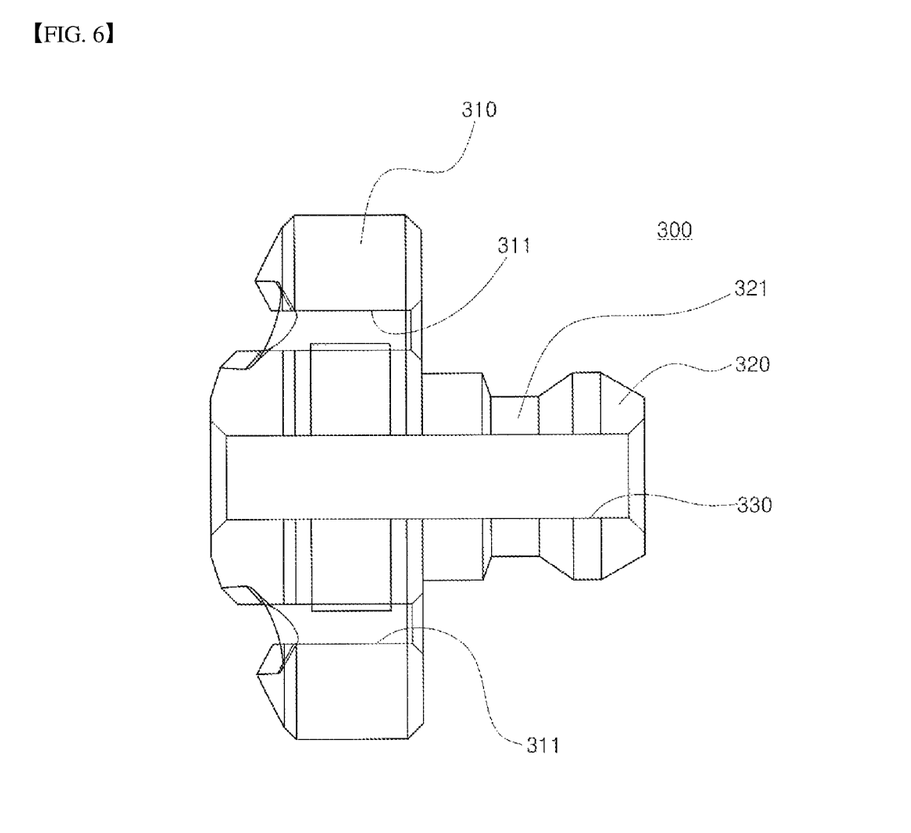
FIG. 6 is a cross-sectional view of a fixing cap of an embodiment.
Figure 7:
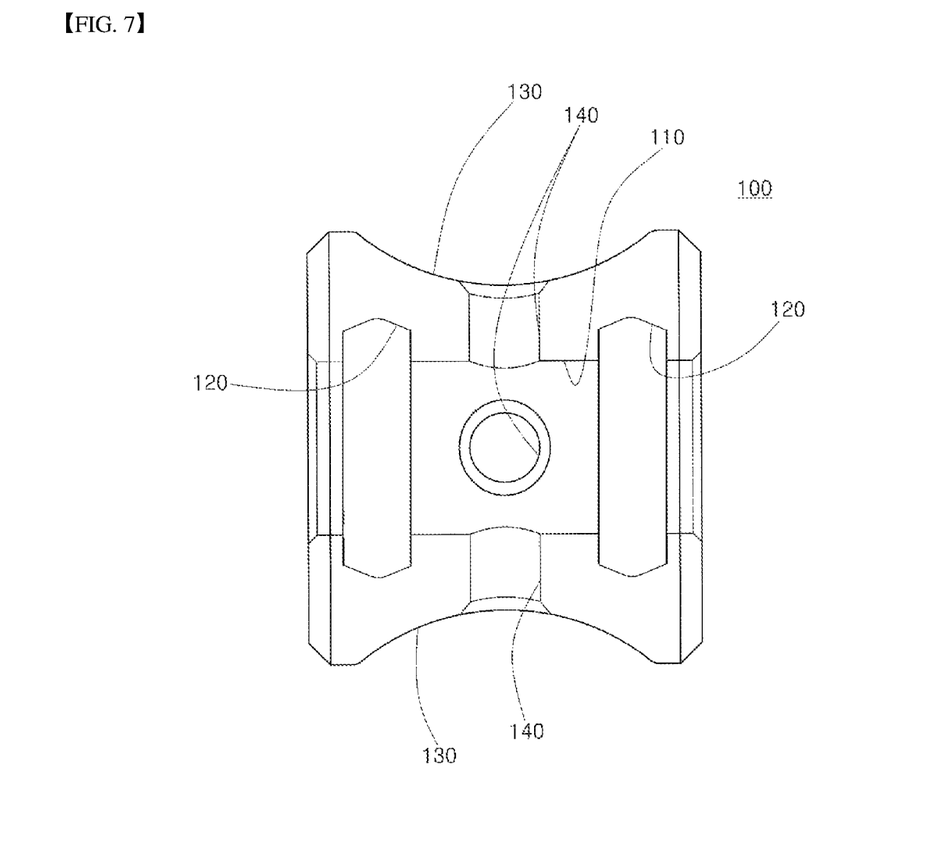
FIG. 7 is a cross-sectional view of a spacer of an embodiment.
Figure 8:
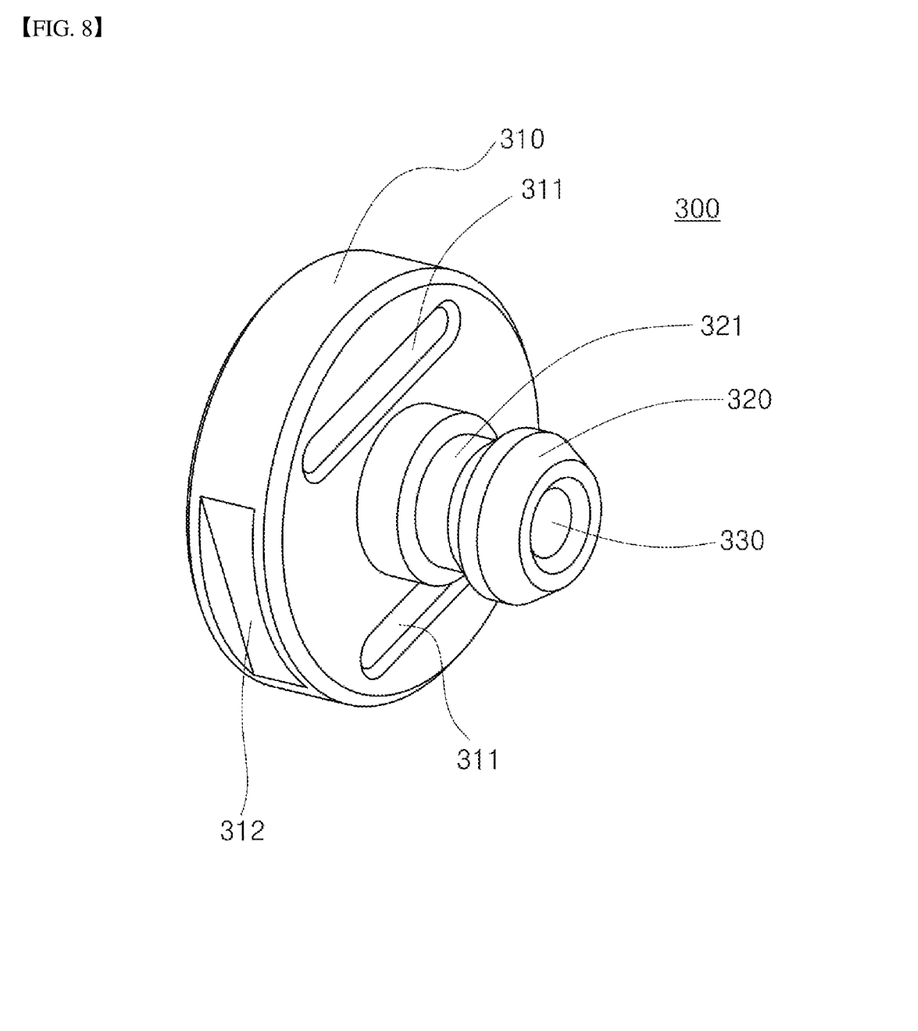
FIG. 8 is a perspective view of a fixing cap of an embodiment.

FIG. 6 is a cross-sectional view of the fixing cap 300 according to an embodiment of the present invention. FIG. 7 is a cross-sectional view of the spacer 100 of an embodiment. FIG. 8 is a perspective view illustrating the fixing cap 300 of an embodiment. Hereinafter, the spacer 100 apparatus between the spinous processes 10 will be described more specifically with reference to FIGS. 1 to 8.

The fixing cap 300 includes a cap body 310 and a coupling part 320. The coupling part 320 and the cap body 310 may be integrally formed.

The cap body 310 may have a first through hole 311 through which the end portion of the band 200 is inserted. The coupling part 320 may protrude from the cap body 310 and may be coupled to the spacer 100. Here, an outer diameter of the cap body 310 may be larger than an outer diameter of the coupling part 320.

The spacer 100 may have a second through hole 110 through which the coupling part 320 is inserted. The second through hole 110 may be formed to penetrate through the spacer 100 in a longitudinal direction of the spacer 100, and thus, a pair of cap bodies 310 may be coupled to the spacer 100 through both ends of the second through holes 110, respectively.

Referring to FIGS. 3 to 6, the first through hole 311 may have a slit shape and may be formed to penetrate through the cap body 310. Also, the first through hole 311 may be formed in a direction parallel to the longitudinal direction of the coupling part 320 and may be formed as a pair symmetrical to each other with respect to the coupling part 320.

One end portion of each of the pair of bands 200 may be inserted into the pair of first through holes 311, and thus, both end portions of the pair of bands 200 may be inserted into a total of four through holes formed in the pair of cap bodies 310.

Referring to FIGS. 3 to 5, when the band 200 is fixed to the spacer 100, the end portion of the band 200 may be inserted into the first through hole 311 and disposed between the spacer 100 and the fixing cap 300.

Here, one surface of the band 200 is in contact with one surface of the spacer 100 and the other surface of the band 200 is in contact with one surface of the fixing cap 300, so that the band 200 may be pressed by the spacer 100 and the fixing cap 300 so as to be coupled to the spacer 100.

That is, the band 200 is maintained in a state of being coupled with the spacer 100 by a pressing force transmitted from one surface of the spacer 100 and one surface of the fixing cap 300 which are in contact with the band 200 and oppose each other and the pressing force maintaining the coupling is provided by coupling of the fixing cap 300 and the spacer 100.

The end portion of the band 200 is inserted into the first through hole 311 and bent so as to be in contact with one surface of the spacer 100 and one surface of the fixing cap 300, whereby the band 200 may be firmly coupled with the spacer 100 when the spacer 100 and the fixing cap 300 are coupled.

Referring to FIGS. 6 and 7, the spacer 100 may have a first groove 120 and the fixing cap 300 may have a second groove 321.

That is, the spacer 100 may include the first groove 120 formed in a circumferential direction on an inner circumferential surface of the second through hole 110 allowing the elastic body 400 to be seated thereon. Here, the elastic body 400 may be manufactured to be coupled to the spacer 100 in a state in which the elastic body 400 is disposed at a position of the first groove 120. Thus, in a state in which the spacer 100 and the fixing cap 300 are separated, the elastic body 400 may be maintained in a state of being coupled to the spacer 100.

The fixing cap 300 may include the second groove 321 formed in a circumferential direction on an outer circumferential surface of the coupling part 320 and face the first groove 120 when the coupling part 320 is inserted into the second through hole 110.

When the spacer 100 and the fixing cap 300 are coupled to each other, the first groove 120 and the second groove 321 face each other, and the elastic body 400 may be disposed in a space formed by the first groove 120 and the second groove 321.

Referring to FIG. 8, the fixing cap 300 may include a guide recess 312 as a portion where a surgical tool (not shown) grips the fixing cap. The guide recess 312 may be formed by being recessed a part of the cap body 310. And the guide recess 312 may be provided as a pair.

In the perspective view of FIG. 8, only one guide recess 312 is illustrated in the cap body 310 but another guide recess 312 may also be formed at a symmetrical position of the fixing cap on the opposite side of the illustrated guide recess 312, so that the guide recesses 312 may be provided as a pair formed at mutually symmetrical positions in the fixing cap 300.

The spacer 100 apparatus between the spinous processes 10 may be mounted on an affected part of the patient by surgery. Here, the fixing cap 300 may be coupled to the spacer 100, or conversely, the fixing cap 300 may be separated from the spacer 100. The guide recess 312 may be formed on the fixing cap 300 so that a surgical tool for gripping the fixing cap 300 may stably and easily grip the fixing cap 300.

Since an outer circumferential surface of the cap body 310 in the fixing cap 300 has a substantially circular shape in cross section, the guide recess 312, which is a planar portion, may be formed as a pair on the cap body 310 and the surgical tool may grip the guide recesses 312 to move the fixing cap 300.

Accordingly, an operator may stably and easily grip the fixing cap 300 using the surgical tool and couple the fixing cap 300 to the spacer 100 or to separate the fixing cap 300 from the spacer 100 conveniently.

Referring to FIGS. 6 and 8, the fixing cap 300 may include a third through hole 330 formed to penetrate through a central portion thereof in a longitudinal direction. The third through hole 330 will be described in detail hereinafter.

Referring to FIG. 7, the spacer 100 may include a fourth through hole 140 and a seating recess 130. The fourth through hole 140 may be formed at the center of the spacer 100 in a diameter direction of the spacer 100, and thus, the third through hole 330 and the second through hole 110 may communicate with each other.

Accordingly, the operator may observe the inside of the spacer 100 through the fourth through hole 140, whereby the operator may examine whether the coupling part 320 of the fixing cap 300 is appropriately inserted into the spacer 100 or whether a guide wire 500 (to be described later) is at an appropriate position, and the like.

The fourth through hole 140 may be provided in an appropriate number in the spacer 100 and, more preferably, the fourth through hole 140 may be provided at the center of each of the seating recesses 130, so that the fourth through hole 140 may be provided to correspond to the number of the plurality of seating recesses 130.

The spinous process 10 may be seated in the seating recess 130. That is, the spacer 100 may have the seating recess 130 provided as a pair at symmetrical positions on an outer circumferential surface thereof and allowing the mutually neighboring spinous processes 10 to be seated thereon, respectively.

Referring to FIGS. 1, 3, and 7, the seating recess 130 may be formed such that the outer circumferential surface of the spacer 100 is depressed at a central portion of the spacer 100, and the seating recess 130 may have an overall gentle curve.

Since the outer circumferential surface of the spacer 100 is generally circular in cross-section, when the spacer 100 is mounted in the patient's body, contact areas of the neighboring spinous processes 10 respectively in contact with the outer circumferential surfaces of the spacer 100 may be small.

Thus, in order to increase the contact areas between the spinous processes 10 and the spacer 100 at the contact portions between the spinous processes 10 and the spacer 100, the seating recess 130 may be formed. Thus, since the spinous processes 10 are seated on the seating recesses 13, the spinous processes 10 may be in contact with a larger contact area of the spacer 100, and thus, the spacer 100 may stably maintain a position between the mutually neighboring spinous processes 10.

Figure 9:
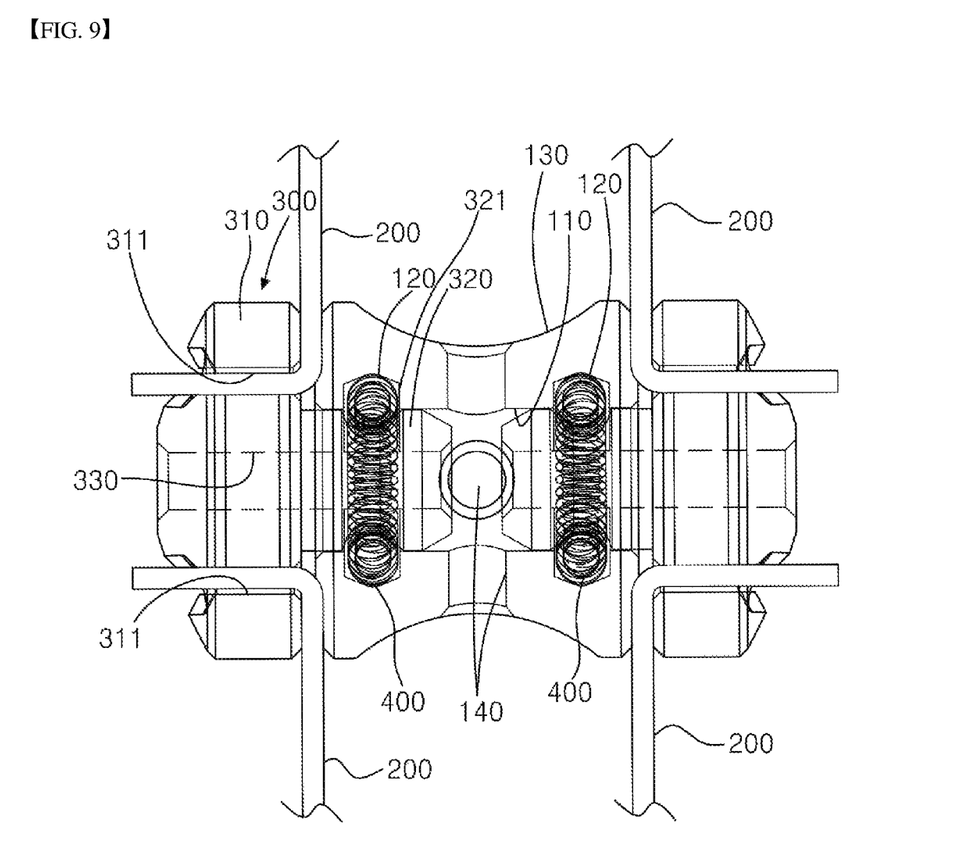
FIG. 9 is a cross-sectional view illustrating a spacer apparatus between spinous processes of an embodiment.

FIG. 9 is a cross-sectional view illustrating a spacer 100 apparatus between spinous processes 10 of an embodiment. When the fixing cap 300 and the spacer 100 are coupled to each other, the end portion of the band 200 is inserted into the first through hole 311 and is sandwiched between the fixing cap 300 and the spacer 100 so as to be coupled with the spacer 100.

Here, the end portion of the band 200 is inserted into the first through hole 311 and is disposed in the longitudinal direction of the spacer 100 and bent in the diameter direction of the spacer 100 so as to be sandwiched between the fixing cap 300 and the spacer 100, and when the fixing cap 300 is coupled to the spacer (100), the end portion of the band 200 is firmly coupled to the spacer 100.

If the end portion of the band 200 is sandwiched between the fixing cap 300 and the spacer 100, without being inserted into the first through hole 311, a portion where the band 200 is in contact with the spacer 100 and the fixing cap 300 is very small.

In this structure, in order to maintain the coupling between the band 200 and the spacer 100, the spacer 100 and the fixing cap 300 must be fastened to have a very strong coupling force. Although the coupling force between the fixing cap 300 and the spacer 100 is strong, if the spinous processes 20 move to continuously apply tension to the band 200, the coupling between the band 200 and the spacer 100 may be loosened or the band 200 may be separated from the spacer 100.

Therefore, in the embodiment, the end portion of the band 200 is inserted into the first through hole 311 and bent to be disposed the spacer 100 and the fixing cap 300, whereby a contact area in which the band 200 is in contact with the fixing cap 300 and the spacer 100 may be increased to increase a coupling force between the band 200 and the spacer 100.

According to the structure of the embodiment described above, it is possible to firmly couple the band 200 and the spacer 100 with a relatively small coupling force, and although the band 200 is continuously tensioned, the solid coupling between the band 200 and the spacer 100 may be maintained.

The elastic body 400 may have a ring shape overall so as to be seated in a space formed by the first groove 120 and the second groove 321.

Referring to FIG. 9, the elastic body 400 may have a circular cross-section. Accordingly, when the coupling part 320 is pushed into the second through hole 110 by pressing the fixing cap 300 in the longitudinal direction of the spacer 100 by the predetermined force or greater, the elastic body 400 is deformed and a front portion of the coupling part 320 passes through the elastic body 400, and as the elastic body 400 is positioned at the second groove 321, the fixing cap 300 is coupled to the spacer 100, and accordingly, the band 200 may be coupled to the spacer 100. Here, the front portion of the coupling part 320 refers to a portion from a front end of the coupling part 320 to the second groove 321.

Conversely, when the fixing cap 300 is pulled by the predetermined force or greater in the longitudinal direction of the spacer 100 in a state in which the fixing cap 300 and the spacer 100 are coupled, the elastic body 400 is deformed and the front portion of the coupling part 320 may pass through the elastic body 400, the fixing cap 300 may be separated from the spacer 100, and accordingly, the band 200 may be separated from the spacer 100.

Referring to FIGS. 6 and 8, a sloped surface, i.e., a chamfered surface, may be formed on the front portion of the coupling part 320 and a side surface of the second groove 321 so that the elastic body 400 presses or pulls the fixing cap 300.

In a case where the coupling part 320 is inserted into the second through hole 110, when the fixing cap 300 is pressed by the predetermined force (e.g., 50N to 70N as described above) or greater, the elastic body 400 is deformed and the front portion of the coupling part 320 may pass through the elastic body 400 so that the fixing cap 300 and the spacer 100 may be coupled.

Here, the elastic body 400 may press the coupling part 320 and the spacer 100 to maintain the coupling force between the fixing cap 300 and the spacer 100. That is, the elastic body 400 is in close contact with the coupling part 320 and the spacer 100 and presses the coupling part 320 and the spacer 100 so that the fixing cap 300 and the spacer 100 may be maintained in a tightly coupled state.

Of course, when the fixing cap 300 is pulled by the predetermined force (e.g., 50N to 70N as described above) or greater, the elastic body 400 is deformed, the front portion of the coupling part 320 may pass through the elastic body 400, and the fixing cap 300 and the spacer 100 may be separated from each other.

In an embodiment, the band 200 may be coupled to the spacer 100, or conversely, separated from the spacer 100 by a simple operation of pressing or pulling the fixing cap 300. Therefore, the spacer 100 apparatus between the spinous processes 10 of the embodiment may simplify a surgical procedure as compared with a device having other similar functions, increasing accuracy and a success rate of surgery.

Figure 10:
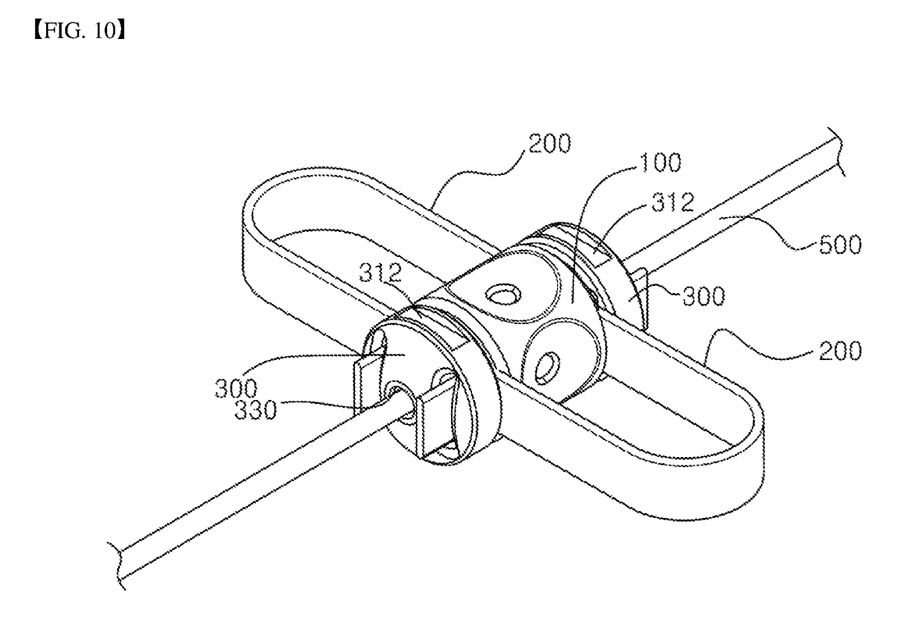
FIG. 10 is a cross-sectional view illustrating a spacer apparatus between spinous processes of another embodiment.

FIG. 10 is a cross-sectional view illustrating a spacer 100 apparatus between the spinous processes 10 of another embodiment. In the embodiment, the spacer 100 apparatus between the spinous processes 10 may further include a guide wire 500.

That is, the fixing cap 300 may include a third through hole 330 formed to penetrate through the center of the cap body 310 and the coupling part 320. Here, the spacer 100 apparatus between the spinous processes 10 may further include the guide wire 500 disposed to be inserted into the second through hole 110 and the third through hole 330.

Here, the guide wire 500 may be slightly thicker so as to be suppressed in elastic deformation so that the operator may move the guide wire 500 to adjust positions of the spacer 100 and the fixing cap 300 between the spinous processes 10.

The guide wire 500 may be inserted to penetrate through the central portions of the fixing cap 300 and the spacer 100 in the longitudinal direction thereof. The guide wire 500 may facilitate, for example, arrangement, coupling, or separation of the fixing cap 300 and the spacer 100.

For example, the fixing cap 300 and the spacer 100 may be inserted into the guide wire 500, the spacer 100 may be disposed at an appropriate position between the mutually neighboring spinous processes 10 by moving the wire and the spacer 100, the end portion of the band 200 may be inserted into the first through hole 311, and the fixing cap 300 may be pressed to be coupled to the spacer 100 to couple the band 200 to the spacer 100.

In an embodiment, when surgery is performed using the guide wire 500, the surgery may be performed more easily as compared with a case where the guide wire 500 is not used. As a result, accuracy and a success rate of the surgery may be further increased.

Meanwhile, after completing the surgery of mounting the spacer 100 apparatus between the spinous processes 10 is mounted in the patient's body, the guide wire 500 may be removed from the spacer 100 apparatus between the spinous processes 10, if necessary.

While only a few have been described above in connection with the embodiments, various other forms may be implemented. The technical contents of the above-described embodiments may be combined in various forms as long as they are not incompatible, and may be implemented in a new embodiment.

In the embodiment, the band may be coupled to the spacer, or conversely, the band may be separated from the spacer, by a simple operation of pressing or pulling the fixing cap. Therefore, the spacer apparatus between the spinous processes of the embodiment may simplify a surgical procedure, as compared with any other device having similar functions, thus improving accuracy and a success rate of surgery.

In the embodiment, when surgery is performed using the guide wire, the surgery may be performed more easily, as compared with a case where the guide wire is not used, and thus, the accuracy and the success rate of the surgery may be further increased.

What is claimed is:

1. A spacer apparatus for implantation between spinous processes, comprising:
    a spacer disposed between two mutually neighboring spinous processes of vertebrae;
    a band provided as a pair, bound respectively to the two mutually neighboring spinous processes and fixed to the spacer in end portion thereof to maintain the spacer between the two mutually neighboring spinous processes;
    a fixing cap coupled to the spacer to fix the end portion of the band to the spacer; and
    an elastic body mounted on the spacer and maintaining a coupling force between the spacer and the fixing cap,
    wherein the fixing cap includes:
    a cap body having a first through hole allowing the end portion of the band to pass therethrough; and
    a coupling part protruding from the cap body and coupled to the spacer, wherein the spacer has a second through hole allowing the coupling part to be inserted thereinto;
    wherein the band is disposed between the spacer and the fixing cap as the end portion thereof is inserted into the first through hole, and is pressed by the spacer and the fixing cap so as to be coupled to the spacer in a state in which one surface of the band is in contact with one surface of the spacer and the other surface thereof is in contact with one surface of the fixing cap.

2. The spacer apparatus of claim 1, wherein
the first through hole has a slit shape, penetrates through the cap body, is formed to be parallel to a longitudinal direction of the coupling part, and is provided as a pair symmetrical to each other with respect to the coupling part.

3. The spacer apparatus of claim 1, wherein:
the spacer includes a first groove formed on an inner circumferential surface of the second through hole in a circumferential direction and allowing the elastic body to be seated therein, and
the fixing cap includes a second groove formed on an outer circumferential surface of the coupling part in the circumferential direction and facing the first groove when the coupling part is inserted into the second through hole.

4. The spacer apparatus of claim 3, wherein:
the elastic body has a ring shape so as to be seated in a space formed by the first groove and the second groove, and
when the coupling part is inserted into the second through hole, the elastic body presses the coupling part and the spacer to maintain a coupling force between the fixing cap and the spacer.

5. The spacer apparatus of claim 1, wherein
the fixing cap includes a guide recess as a portion where a surgical tool grips the fixing cap, wherein the guide recess is formed by being recessed a part of the cap body, and the guide recess is provided as a pair.

6. The spacer apparatus of claim 1, wherein
the spacer has a seating recess provided as a pair at symmetrical positions on an outer circumferential surface thereof and allowing the mutually neighboring spinous processes 10 to be seated thereon, respectively.

7. The spacer apparatus of claim 1, wherein:
the fixing cap includes a through hole formed to penetrate through the centers of the cap body and the coupling part, and
the spacer apparatus between spinous processes further comprising:
a guide wire disposed to be inserted into the second through hole and the third through hole.

* * * * *